United States Patent [19]

Heinecke

[11] Patent Number: 4,499,896

[45] Date of Patent: Feb. 19, 1985

[54] RESERVOIR WOUND DRESSING

[75] Inventor: Steven B. Heinecke, New Richmond, Wis.

[73] Assignee: Minnesota Mining and Manufacturing Co., St. Paul, Minn.

[21] Appl. No.: 363,609

[22] Filed: Mar. 30, 1982

[51] Int. Cl.³ .............................................. A61F 13/00
[52] U.S. Cl. .................................................. 128/156
[58] Field of Search ................... 128/155, 156, 132 D, 128/132 R, 151, 760, 767; 604/304, 344, 307, 355, 356, 357, 277, 317, 327, 332, 335, 337, 339, 341, 342

[56] References Cited

U.S. PATENT DOCUMENTS

| | | | |
|---|---|---|---|
| 1,956,695 | 5/1934 | Reinitz | 128/155 |
| 1,967,923 | 7/1934 | Connolly | 128/268 |
| 2,893,388 | 7/1959 | Ganz | 128/156 |
| 2,923,298 | 2/1960 | Dockstader et al. | 128/296 |
| 3,018,881 | 1/1962 | Wall | 206/56 |
| 3,055,368 | 9/1962 | Baxter | 604/344 |
| 3,073,304 | 1/1963 | Schaar | 128/156 |
| 3,285,245 | 11/1966 | Eldredge et al. | 128/156 |
| 3,520,306 | 7/1970 | Gardner | 128/335 |
| 3,521,631 | 7/1970 | Gardner | 128/156 |
| 3,645,835 | 2/1972 | Hodgson | 161/146 |
| 3,658,065 | 4/1972 | Hirsch | 128/296 |
| 3,709,221 | 1/1973 | Riely | 128/156 |
| 3,870,041 | 3/1975 | Davies | 128/156 |
| 3,888,247 | 6/1975 | Stenvall | 128/155 |
| 3,903,882 | 9/1975 | Augurt | 128/155 |
| 3,927,669 | 12/1975 | Glatt | 128/156 |
| 4,181,127 | 1/1980 | Linsky et al. | 128/155 |
| 4,231,357 | 11/1980 | Hessner | 128/156 |
| 4,308,623 | 1/1982 | Voorhees | 128/151 |
| 4,341,207 | 7/1982 | Steer et al. | 128/156 |

FOREIGN PATENT DOCUMENTS

| | | | |
|---|---|---|---|
| 153276 | 9/1953 | Australia | 128/156 |
| 59049 | 9/1982 | European Pat. Off. | 128/156 |
| 648733 | 2/1951 | United Kingdom | 128/156 |

OTHER PUBLICATIONS

G. D. Winter, "Healing of Skin Wounds and the Influence of Dressings on the Repair Process", *Surgical Dressings and Wound Healing, Proceedings of a Symposium held on Jul. 7-8, 1970 at the University of Bradford*, ed. Harkiss, pp. 46-60.

Simpson et al., "A Method of Studying the Performance of Dressings Using a Standard Wound in the Domestic Pig", Surgical Dressings and Wound Healing, Proceedings of a Symposium held on Jul. 7-8, 1970 at the University of Bradford, ed. Harkiss, pp. 70-77.

U.S. Application Ser. No. 205,344, filed Nov. 10, 1980, entitled "Device and Method of Applying Conformable Thin Adhesive-Coated Films".

*Primary Examiner*—Henry J. Recla
*Assistant Examiner*—Karin M. Reichle
*Attorney, Agent, or Firm*—Donald M. Sell; James A. Smith; Carolyn A. Bates

[57] ABSTRACT

A wound dressing for wounds having a significant amount of exudate comprising a conformable, moisture vapor-permeable, liquid water-impermeable first layer containing at least one hole therein through which exudate can pass, and an imperforate, conformable, liquid water-permeable, moisture vapor-permeable second layer attached to the first layer and overlaying the hole or holes in the first layer and forming a reservoir into which the wound exudate can pass and from which the exudate can evaporate.

10 Claims, 9 Drawing Figures

RESERVOIR WOUND DRESSING

This invention relates to wound dressings. Particularly this invention relates to wound dressings for use on wounds which are passing a significant amount of wound exudate. More particularly, this invention relates to wound dressings which contain a reservoir into which wound exudate can pass and from which the moisture from the wound exudate can be transmitted.

Historically, exudate from a weeping wound has been dealt with by absorbing it using a dressing containing some type of absorbent material. Examples include dressings such as those shown in U.S. Pat. No. 2,893,388, U.S. Pat. No. 3,018,881 and U.S. Pat. No. 3,073,304. All of these dressings contain a padded absorbent material attached to an adhesive tape backing. The padded absorbent material is applied to the wound to absorb the wound exudate. A difficulty with this type of dressing is that as the wound heals, the scab typically forms in and as part of the pad. Thus, when the dressing is removed, the scab is removed. The disclosures of U.S. Pat. No. 2,923,298, U.S. Pat. No. 3,285,245 and U.S. Pat. No. 3,870,041 have addressed this problem by providing a porous film between the absorbent material and the wound to reduce the likelihood that a scab formed will become attached to the absorbent material U.S. Pat. No. 3,888,247 discloses placing a microporous material over the wound and then applying a perforated urethane film containing a wound dressing made in accordance with U.S. Pat. No. 3,285,245 over the microporous tape applied to the wound. U.S. Pat. No. 1,967,923 contains a cellulose sheet membrane or film which protects the dressing and allows air to circulate over the wound. Other wound dressings comprising films are disclosed in U.S. Pat. No. 3,645,835 and U.S. patent application Ser. No. 205,344, filed by applicant on Nov. 10, 1980, entitled "Device and Method of Applying Conformable Thin Adhesive-Coated Films".

A difficulty with dressings which comprise a thin film applied to the wound involves a pooling of exudate under the film if the wound is producing a large amount of exudate. This can result in loosening or removal of the wound dressing. An attempted solution to this problem is provided in U.S. Pat. No. 1,956,695 which discloses a round plaster which contains a rubber film which expands to allow pus to collect under it. This plaster allows the exudate to remain against the wound. Another attempted solution is provided in U.S. Pat. No. 3,521,631 which discloses an impervious sheet placed over a wound with an absorbent material extending over the impervious sheet and around its edges to allow wound exudate to pass into the absorbent material at the edges of the impervious sheet. This entire structure is covered with a backing sheet which is impervious and occlusive. An alleged improvement of the device disclosed in U.S. Pat. No. 3,521,631 is that disclosed in U.S. Pat. No. 4,181,127. An imperforate film of polyurethane contacts the wound which has an absorbent material over it that overlaps the film edges so that the exudate is passed to the absorbent material at the edges of the film. Adhesive tape can be applied over the top of the combination as long as the moisture vapor transmission of the total construction is at least 0.06 mg/cm²/hour.

A reservoir bandage is disclosed in U.S. Pat. No. 3,658,065. The reservoir contains an absorbent material and is covered on the non-wound contacting surface with an impervious material. U.S. Pat. No. 3,709,221 discloses a device comprising an inner macroporous fibrous layer for contacting the wound, an absorbent intermediate layer, and an outer microporous, liquid repellent fibrous layer. Air can reach from the outside into the absorbent layer to dry the exudate. A germicide can be included. The microporous outerlayer passes moisture by open pores, not by a diffusion process, but does not pass liquid. The inner macroporous layer is to pass liquid easily.

U.S. Pat. No. 3,903,882 discloses an exterior surface of polyurethane, silicone, poly(caprolactone) or natural rubber which has a moisture vapor permeability like human skin. Attached to the film on the wound contacting surface is a knitted fabric which is compatible with and absorbable by the human body.

Applicant has discovered a wound dressing (1) which covers the wound in a nonocclusive but liquid water impermeable fashion, (2) allows wound exudate to pass from the surface of the wound into a reservoir, (3) allows the exudate from the wound to dry in the reservoir by passage of moisture vapor therefrom yet allows the wound to heal under moist conditions without significant scab formation, (4) does not provide pathways for passage of bacteria to the wound, and (5) does not cause significant skin maceration under the wound dressing. Specifically, applicant has discovered a wound dressing comprising:
 (a) a first layer for placing over a wound which is conformable to animal anatomical surfaces, has a moisture vapor permeability of at least 300 grams per square meter per 24 hours at an 80% relative humidity differential at 40° C., is impermeable to liquid water throughout substantially its entire imperforate area, and contains perforation means for passing wound exudate through said first layer, and
 (b) a second layer which is imperforate, is conformable to animal anatomical surfaces, is impermeable to liquid water, and has a moisture vapor permeability of at least 600 grams per square meter per 24 hours at an 80% relative humidity differential at 40° C., said second layer overlaying said perforation means of said first layer and being attached to said first layer on the side opposite to that which contacts the wound and in an area surrounding said perforation means to provide a reservoir into which exudate from a wound can pass and be at least partially evaporated therefrom.

Normally, the wound dressing will contain a pressure sensitive adhesive on the wound contacting surface of the first layer to attach the wound dressing to the wound.

Applicant has also discovered a method for treating wounds comprising applying the device comprising the wound dressing discussed above to a wound, allowing the wound exudate to pass through the perforation means of the first layer of said wound dressing into the reservoir and allowing moisture vapor from said exudate to escape from said wound dressing by passing through said second layer.

Moisture vapor permeability referred to herein and in the claims except as otherwise noted refers to moisture vapor permeability determined in accordance with the following method:
 (1) cut a 1.25 inch (3.17 cm) diameter sample of material to be tested containing no perforations,
 (2) fill a container half full of water, (3) place the sample on top of the container so that a 1 inch (2.54 cm) diameter (0.785 in$^2$) (5.06 cm$^2$) area is being tested, (4) weigh the assembly, (5) place the assembly in a circulation oven set at 40° C. and 20% relative humidity for 48 hours, (6) remove the assembly and weigh, and (7) calculate the water loss in g/m$^2$/24 hours at 80% relative humidity differential at 40° C.

Impermeable to liquid water as used herein means impermeable to liquid water under normal wound treatment conditions.

Applicant's method and device comprising a wound dressing will be discussed in more detail with reference to the drawings.

Figure 1:
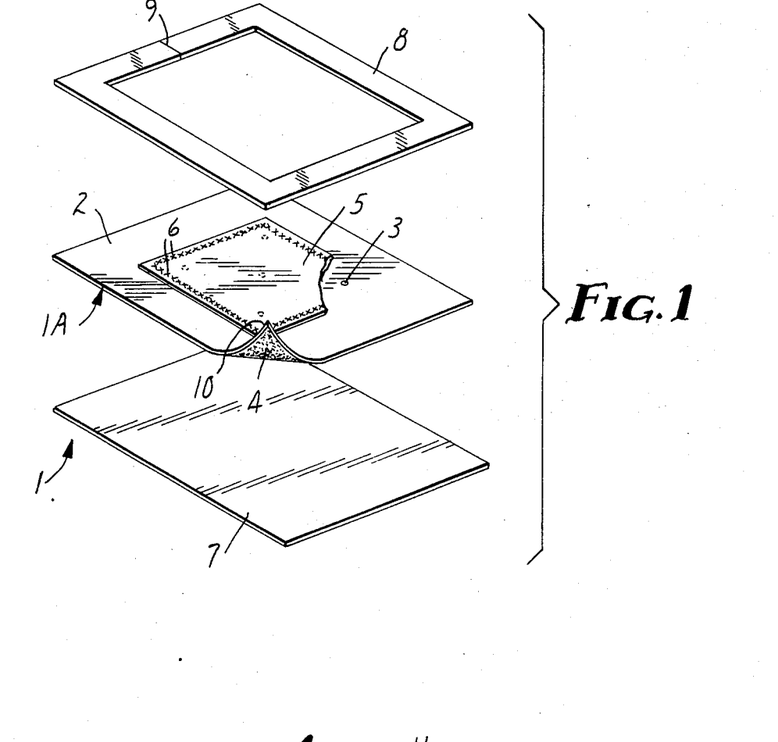
FIG. 1 is an exploded perspective view of one embodiment of the invention.

Referring to the drawings in more detail, FIG. 1 is an exploded perspective of one embodiment of the device of the present invention comprising wound dressing 1A. Wound dressing 1A comprises first layer 2 containing perforations 3 and having one surface thereof covered with pressure-sensitive adhesive 4. The perforations 3 in first layer 2 are covered by second layer 5. Second layer 5 is attached to first layer 2 by means of seal 6, which extends around the entire periphery of second layer 5. Adhesive 4 of first layer 2 is covered by release liner 7 before use. Attached to first layer 2 on the surface opposite to that containing the pressure-sensitive adhesive 4 is frame 8 which contains slit 9. Frame 8 allows the wound dressing 1A to be applied easily to a wound and then is removed by pulling on frame 8 at slit 9. This is described in more detail in U.S. patent application Ser. No. 205,344, filed Nov. 10, 1980, by applicant, and entitled "Device and Method of Applying Conformable Thin Adhesive-Coated Films".

Figure 2:
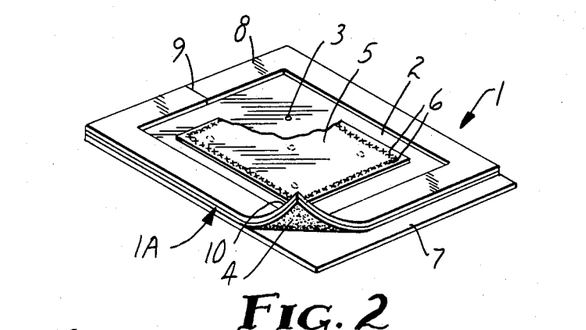
FIG. 2 is a perspective view of the embodiment shown in FIG. 1 with some parts broken away.

Device 1 is depicted in FIG. 2 as it would be prior to use. All portions are attached with only corner 10 being upturned to show adhesive 4 on the surface of first layer 2 on corner 10. It can also be seen in FIG. 2 that release liner 7 extends beyond first layer 2 and frame 8 to allow for easy grasping and removal of release liner 7 from the adhesive 4 of first layer 2.

Figure 3:
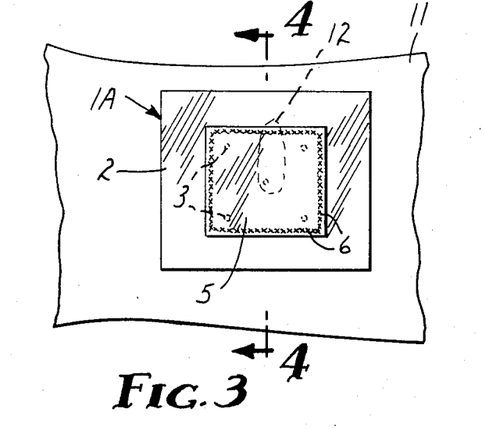
FIG. 3 is a plan view of the embodiment of the present invention shown in FIGS. 1 and 2 placed on a wound on the arm of a patient.

FIG. 3 shows wound dressing 1A on arm 11 and covering wound 12. Wound dressing 1A is applied to arm 11 over wound 12 by removing release liner 7 (FIG. 1) from wound dressing 1A and placing wound dressing 1A utilizing frame 8 (FIG. 1) on wound 12 on arm 11. Wound dressing 1A remains affixed to arm 11 by means of adhesive 4 of first layer 2. Frame 8 (FIG. 1) is removed from wound dressing 1A after wound dressing 1A is applied to arm 11 by means of pulling at slit 9.

Figure 4:
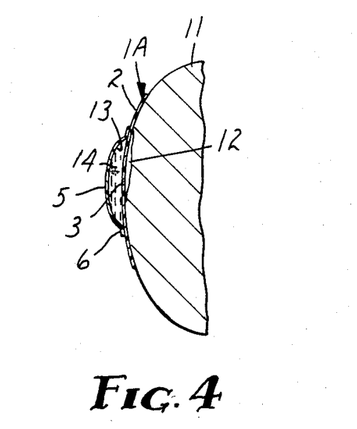
FIG. 4 is a section view taken along line 4—4 of FIG. 3.

One of the perforations 3 in first layer 2 in wound dressing 1A is over wound 12. Exudate from wound 12 can pass through the perforation 3 over wound 12 or can pass through another perforation 3 adjacent thereto. This is shown more graphically in FIG. 4 which shows the section along line 4—4 of FIG. 3. In FIG. 4 it can be seen that wound dressing 1A is attached to arm 11 over wound 12. Wound dressing 1A contains reservoir 13 containing exudate 14 from wound 12. The exudate 14 passes into reservoir 13 by means of perforation 3. Because second layer 5 is expandable, it allows a reservoir 13 to form and expand in size as exudate 14 passes from wound 12 through perforation 3 into reservoir 13. Normally the flow of exudate from the wound will subside in time by means of normal body functions or when an equilibrium is reached between the pressure forcing the exudate from the body and the resistance of the reservoir to further expansion. The moisture from exudate 14 slowly passes through second layer 5 because of the moisture vapor permeability of second layer 5. Seal 6 prevents exudate 14 from escaping in a liquid form from reservoir 13.

Figure 5:
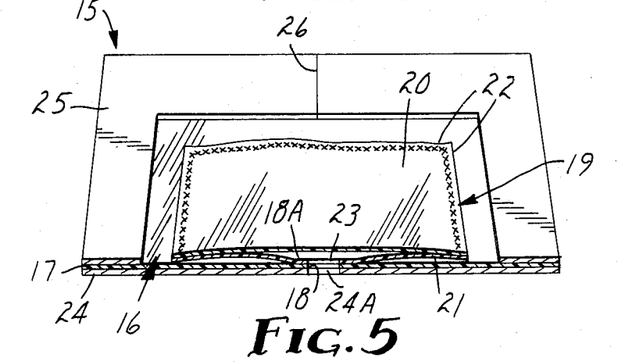
FIG. 5 is a perspective view with parts in section of another embodiment of the present invention.
Figure 6:
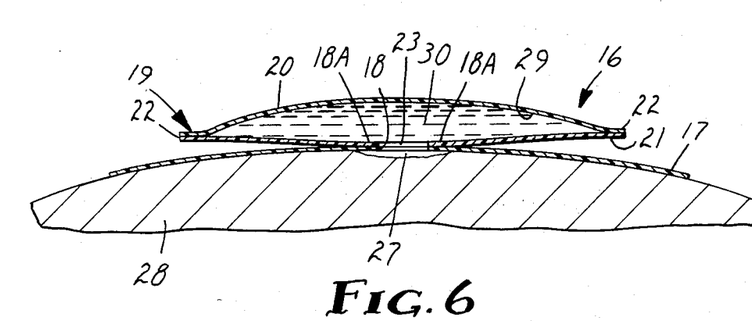
FIG. 6 is a section of the embodiment shown in FIG. 5 on a wound on the body.

FIG. 5 depicts a perspective view in section of another embodiment of the present invention. In this embodiment device 15 comprising wound dressing 16 comprising first layer 17 which contains adhesive (not shown), and perforation 18. First layer 17 is attached to second layer 19 at the periphery 18A of perforation 18 in first layer 17. Second layer 19 comprises upper portion 20 and lower portion 21 which are sealed together around the edges 22 thereof. Second layer 19 contains perforation 23. Attached to the adhesive surface of first layer 17 is release liner 24 containing optional perforation 24A. Attached to the other surface of first layer 17 is frame 25 containing slit 26. In use, release liner 24 is removed and wound dressing 16 is applied over wound 27 (FIG. 6) on body limb 28 utilizing frame 25. Frame 25 is removed by lifting frame 25 at slit 26. Exudate 30 from wound 27 flows into reservoir 29 of second layer 19. Because of the moisture vapor permeability of second layer 19, the moisture from exudate 30 passes through second layer 19 into the atmosphere. Seal 22 and the attachment of second layer 19 around the periphery 18A of perforation 18 in first layer 17 prevents liquid exudate 30 from escaping from reservoir 29.

Figure 7:
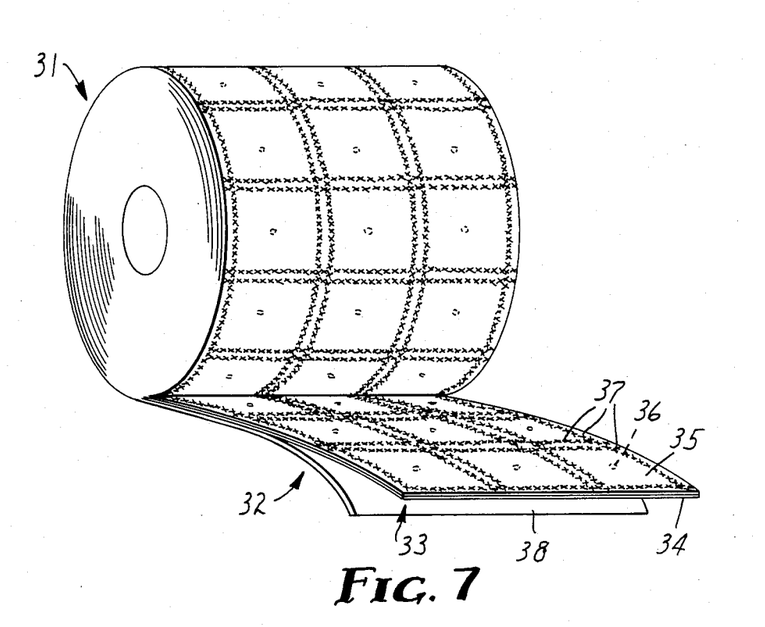
FIG. 7 is a perspective view of a roll of another embodiment of the present invention.
Figures 8, 9:
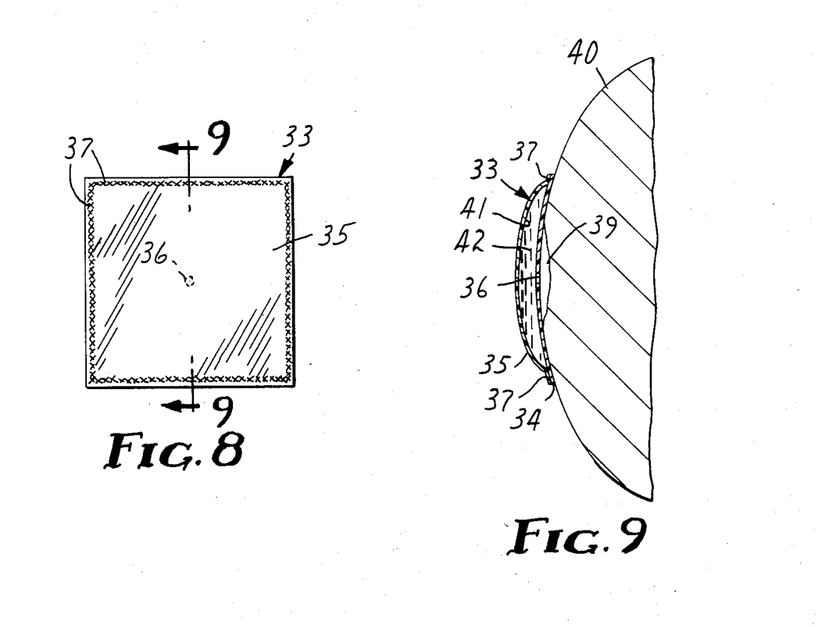
FIG. 8 is a plan view of one portion of FIG. 7.
FIG. 9 is a section view taken along line 9—9 of FIG. 8 showing the wound dressing on a wound on a body.

FIG. 7 depicts another embodiment of the present invention comprising roll 31 of devices 32 comprising wound dressings 33 comprising first layer 34 containing adhesive on one surface thereof (not shown) and containing second layer 35 covering the first layer 34. First layer 34 contains perforations 36. Second layer 35 is attached to first layer 34 by means of seals 37. The seals 37 as shown divide the roll 31 into separate devices 32 and wound dressings 33 across the length and width of the roll 31. To separate the devices 32 and wound dressings 33 from each other one cuts between the seals 37. Single or multiple devices 32 and wound dressings 33 can be cut and used on wounds. A release liner 38 is attached to the adhesive containing side of first layer 34. FIG. 8 depicts one of the wound dressings 33 from roll 31 in plan view. In this view, it can be seen perforation 36 is in the center of first layer 34. Perforation 36 does not pass through second layer 35. The seal 37 which attaches first layer 34 to second layer 35 is shown.

FIG. 9 depicts a section view taken along line 9—9 of FIG. 8 of the wound dressing 33 covering wound 39 on body limb 40 and attached thereto by adhesive of first layer 34. Perforation 36 passes exudate 42 from wound 39 through first layer 34 into reservoir 41 which is between first layer 34 and second layer 35. The exudate 42 is maintained within reservoir 41 by means of seals 37 which attach first layer 34 to second layer 35. The moisture from exudate 42 passes through second layer 35 because of the moisture vapor permeability of second layer 35.

In all of the embodiments of the invention discussed above, a first layer is present. This first layer is conformable to animal (including human) anatomical surfaces, has a moisture vapor permeability of at least 300 grams per square meter per 24 hours at 80% relative humidity differential at 40° C., is impermeable to liquid water throughout substantially its entire imperforate area and contains perforations means for passing wound exudate through the first layer. The preferred moisture vapor permeability is at least 600 grams per square meter per 24 hours at an 80% relative humidity differential at 40° C. The first layer normally comprises a backing and a pressure sensitive adhesive. The composite must have the aforesaid characteristics. Therefore, if the backing is impermeable to liquid water except for the perforation means, the adhesive can be permeable to liquid water and vice versa. Porous backings such as perforated polypropylene, polyethylene, chlorinated polyethylene, styrene/butadiene block copolymers ("Kraton" brand thermoplastic rubber, Shell Chemical Company, Houston, Tex.) and polyvinyl chloride and those described in U.S. Pat. No. 3,121,021 which are covered with a pressure sensitive adhesive which is not permeable to liquid water can be used for the first layer. The second layer is then attached to the first layer so that the second layer is attached through the backing of the first layer directly to the pressure sensitive adhesive to provide a reservoir which is sealed except for the perforation means which allows the wound exudate to enter the reservoir.

The first layer is impermeable to liquid water throughout substantially its entire imperforate area. This means that the first layer does not pass liquid water under normal wound treatment conditions except at the places in the first layer which are positively perforated to allow the exudate to pass into the reservoir.

It is required that the first layer have the above mentioned moisture vapor permeability (1) so that maceration of the skin under the wound dressing does not occur, (2) so that moisture build-up under the first layer does not cause the first layer and, therefore, wound dressing to be lifted off the skin, and (3) to enhance proximation of the wound edges. Preferred first layers are discussed in more detail below in reference to the second layer. These are thin polymeric films coated with pressure sensitive adhesive which, in combination, have the above characteristics.

The perforation means in the first layer are holes or slits or other perforations which do not significantly impede the passage of liquid water or wound exudate from the wound into the reservoir of the wound dressing.

The second layer is also present in all of the embodiments of the present invention. It is imperforate, conformable to animal anatomical surfaces, impermeable to liquid water and has a moisture vapor permeability of at least 600 grams per square meter per 24 hours at an 80% relative humidity differential at 40° C. The second layer forms a reservoir into which the exudate from the wound passes. As noted, this reservoir does not permit liquid water or exudate to pass out of it. Instead, the moisture in the exudate passes through the second layer in a vapor form into the atmosphere. The reservoir permits wound exudate to be rapidly removed from the wound site and then to dry in an environment which does not provide a pathway for bacteria to the wound and is effectively sealed except for the passage of the vapor therefrom.

In order to accomodate the required removal of moisture vapor the moisture vapor permeability of the second layer is at least as above noted, and preferably at least 1200 grams per square meter per 24 hours at an 80% relative humidity differential at 40° C.

It is preferred that the second layer be easily expanded or stretched to accomodate the wound exudate as it passes into the reservoir. This provides a reservoir which is capable of increasing in size as the circumstances demand. In this regard, it is much preferred that the second layer be a thin polymeric film which will be described in more detail below. Alternatively, the second layer can be a porous backing such as that described in U.S. Pat. No. 3,121,021 or alone in respect to the first layer with an imperforate pressure sensitive adhesive attached thereto having the above noted moisture vapor permeability. The pressure sensitive adhesive would, in that event, normally be on the side of the backing adjacent to the first layer although it could be on the other side. The pressure sensitive adhesive would normally be covered with a material to impede its adhesive properties so that it would not stick to garments if it is on the outside of the reservoir or to the first layer except at the periphery if on the inside of the reservoir. Absorbent material can be used in the reservoir to reduce the adhesive properties of the adhesive if it is on the inside surface of the second layer.

The preferred embodiments for the first and second layers are thin conformable polymeric films. Generally the films are from 12 to 50 microns in thickness, preferably from 12 to 25 microns. Conformability is somewhat dependent on thickness, thus the thinner the film the more conformable the film. Reference has been made herein to the films utilized in the wound dressing of the present invention being conformable to animal anatomical surfaces. This means that when the films of the present invention are applied to an animal anatomical surface, it conforms to the surface even when the surface is moved. The preferred films are conformable to animal anatomical joints. When the joint is flexed and then returned to its unflexed position, the film stretches to accomodate the flexation of the joint but is resilient enough to continue to conform to the joint when the joint is returned to its unflexed condition. A measure of conformability is the $F_{10}$ modulus of the film which is the pounds (grams) force it takes to stretch a material ten percent of its original length. The preferred films of the present invention preferably have a $F_{10}$ modulus no greater than about 1 pound (454 grams) and preferably less than about 0.8 pounds (363 grams). The wound dressing of the present invention can be utilized on films which have $F_{10}$ moduli upwards of 2.5 pounds (1135 grams), However, as the $F_{10}$ modulus increases, the conformability decreases, and the ability to handle the films without the films sticking to themselves is increased.

$F_{10}$ modulus as referred to herein is determined using an Instron Unit Model 1102 from Instron Corp., 2500 Washington St., Canton, Mass. The cross-head speed of the Instron is ten inches per minute and the chart speed is set at ten inches (25.4 cm) per minute. The gauge length is set at two inches (5 cm) with the test sample cut to test a one-inch width (2.54 cm.).

Examples of films which are useful in applicant's invention include polyurethane, elastomeric polyester such as "Hytrel" polyester elastomer (E. I. duPont deNemours & Co., Wilmington, Del.), blends of polyurethane and polyester, and polyvinyl chloride. Particularly preferred films for use in the present invention are polyurethane and elastomeric polyester films. The polyurethane and elastomeric polyester films exhibit a resilient property which allows the film to have good conformability and to expand to form a reservoir which will increase in size. However, the resilient property also causes them to compress the tissue if the film is applied under tension onto the wound site, i.e., if the film is in a stretched condition when it is placed on the wound. Thus, it is preferred with those films and other films which exhibit a significant degree of resiliency to use the frame described in reference to the drawings.

It is preferred that the first and second layers of the present invention be at least translucent and more preferably transparent so that the wound site to which they are applied can be viewed through them. It is preferred that both the first layer and second layer be one of the films discussed above. While the first layer can be attached to the wound by means other than a pressure sensitive adhesive on its surface, it is preferred to use such an adhesive. The presence of the adhesive of the first layer normally reduces the moisture vapor permeability of the first layer. Thus the moisture permeability both generally and preferably is normally higher for the second layer than the first layer since the second layer preferably does not contain pressure sensitive adhesive.

The first layer is normally attached to the wound by means of adhesive which can be continuous or pattern coated. The preferred adhesive which can be used with the wound dressings of present invention are the normal adhesives which are applied to the skin such as those described in Ulrich U.S. Pat. No. Re. 24,906, particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 which comprise block copolymers having three or more polymer block structures having a general configuration--A--B--A---wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are iso-octyl acrylate/n-vinyl pyrrolidone copolymer adhesives and crosslinked acrylate adhesives such as for example those described in U.S. Pat. No. 4,112,213. Inclusion in the adhesive of medicaments is useful for enhancing wound healing and the inclusion of antimicrobial agents such as iodine is useful for preventing infection.

The release liner which is attached to the adhesive of the first layer is a liner which releases with less force than is required for the frame or releasable layer to be removed from the first layer. Generally, the adhesion to the liner as determined in accordance with ASTM D3330-76 is between about 3 and 20 grams per 2.54 cm width while the adhesion to releasable layer of the first layer is greater than that to the liner and ranges up to about 70 grams per 2.54 cm width if the first layer is a thin, polymeric film as above described. Examples of release liners are liners made of or coated with polyethylene, polypropylene and fluorocarbons and silicone coated release papers or polyester films. Examples of the silicone coated release papers are Polyslik S-8004, 83 pound (135.4 g/m$^2$) bleached silicone release paper supplied by H. P. Smith Co., Chicago, Ill., and 80 pound (130.5 g/m$^2$) bleached two-sided silicone coated paper (2-80-BKG-157) supplied by Daubert Chemical Co., Dixon, Ill.

The frames or releasable layers normally comprise materials which will adhere to the first layer and with a greater tenacity than release liners adhere to the adhesives in order that the release liners are removed prior to the removal of the releasable layers. The releasable layers can comprise materials generally of the type described in respect to the release liner although the more adherent varieties or surfaces of the above materials will be used as releasable layers. The releasable layers are attached with less tenacity to the first layer than the adhesive attaches the first layer to the animal anatomical surface.

The first and second layers of the wound dressings of present invention are attached to each other, as well as the upper and lower layers of the second layer of the wound dressing of FIG. 5 by conventional means such as by adhesives, heat sealing or other bonding techniques. The preferred method is by heat bonding.

The reservoir provided in the wound dressings of the present invention can but need not include within it absorbent materials such as absorbent powders (such as dextran or starch) cotton, gauze or other types of woven or nonwoven fabric which will provide rapid induction of the wound exudate into the reservoir. Also medicaments can be included in the reservoir.

The devices and wound dressings of the present invention are manufactured using conventional film-forming (for example, extrusion, casting or calendaring), web-formation, adhesive placement, slitting and heat sealing or bonding techniques. The method of manufacture of the device of FIG. 1 will be described. A releasable layer which becomes frame 8 is preferably coated with film 2 by means of extruding the polymer through a die onto the releasable layer. Adhesive 4 is then applied to the film 2 to complete the first layer using normal direct or transfer coating techniques. The first layer 2 is slit to the desired width. The release liner 7 is then laminated to the adhesive 4. The releasable layer is then control depth cut to form frame 8 and to form slit 9. The "window" from the releasable layer is removed to leave frame 8 in place on first layer 2. Holes 3 are then punched through first layer 2, including adhesive 4 and release liner 7, although the latter is not necessary. Pre-cut second layer 5 is then placed in proper position over first layer 2 and they are heat sealed together around the periphery of the second layer. The method for making the other embodiments of the present invention utilize the above techniques, and are adapted to achieve the other embodiments as is apparent to one skilled in the art.

The following examples are meant to illustrate but not to limit the invention.

In the following examples, the test for moisture vapor transmission performed on animals was performed as follows:

(1) Turn on Servomed Evaporimeter EP-1 (Servomed, AB, Stockholm, Sweden),
(2) depress the WE and Range buttons, (3) zero machine,
(4) using a screen probe, place directly on sample to be tested,
(5) place chamber over subject as you test to minimize turbulent air, and
(6) wait until digital read out is stable and take moisture vapor transmission (MVT) reading in g/m$^2$/hr at normal room conditions, i.e., approximately 72° F. and 40% relative humidity

EXAMPLE 1

A 0.85 mil (22 micron) film of "Estane" 58309 NAT022 polyurethane resin (B. F. Goodrich, Cleveland, Ohio) was extruded using a two and a half inch (6.4 cm) HPM Torque Master 3 screw extruder (manufactured by HPM Corporation, Mount Gielead, Ohio) utilizing a melt temperature of 200° C. The film was extruded onto the kraft side of a 78 pound (127 grams per m$^2$) paper (releasable layer) which was clay-coated on one side by roll coating (Paper No. 78-05-04-000, Boise Cascade Corporation, International Falls, Minn.). Immediately after the extruder die, the paper/resin combination was passed through a nip roll at 95 psi (6680 g/cm$^2$) wherein the nip comprises a chrome roll at 180° F. and a rubber roll at 90° F. and the releasable layer is against the chrome roll. Twenty-five g/m$^2$ of an adhesive prepared in accordance with U.S. Pat. No. Re. 24,906 comprising a copolymer of 96% units is isooctylacrylate and 4% units of acrylamide was applied to the surface of the film that was not attached to the clay-coated paper utilizing a standard horizontal knife coater. A release liner comprising 80 pounds (130.5 g/m$^2$) bleached, one side coated, silicone paper (2-80 BKG-157, Daubert Chemical Company, Dixon, Ill.) was applied to the adhesive on the film. Samples were prepared having the configuration shown in FIG. 1 using a die cutting machine for control depth die cutting (Model 813, Series K7Y223, Mark Andy, St. Louis, Mo.). The first layer was 4"×4¾" (10 cm×12 cm). The center portion of the releasable layer was removed from the releasable layer and only a frame as shown in FIG. 1 remained as the releasable layer. The adhesive coated film was slit with a razor blade to form 5 perforations spaced in a pattern toward the center of the dressing as shown in FIG. 1. The four corner perforations were 3.8 cm apart, and one perforation was in the center. Each perforation was in the form of crossed slits with the horizontal and vertical portions being ¼" (0.64 cm). A second section of the film (5 cm×5 cm) or second layer as above descried without adhesive was centered on the nonadhesive side of the first layer within the boundaries of the frame, insuring that the film covered the slits. The two sections of film were then heat sealed together using a heat sealer (Model 14PCB Vertrod Corp., Brooklyn, N.Y.) at the outside perimeter of the second piece of film. Samples were tested in vitro and in vivo with the following results:

| water vapor permeability (in vitro) | first layer (singly) | 823 g/m$^2$/24 hr/ 80% relative humidity differential/40° C. |
|---|---|---|
| | second layer (singly) | 1200 g/m$^2$/24 hr/ 80% relative humidity differential/40° C. |

| Moisture Vapor Transmission (in vivo on pig wounds which are split thickness wounds made by Dermatome (2.5 cm × 2.5 cm)) | | | | |
|---|---|---|---|---|
| | | (g/m$^2$/hr) | | |
| Sample Type | Pig | On Placement | 24 Hours | 48 Hours |
| FIG. 1 | 1 | 8.2 | 21.7 | 22.8 |
| FIG. 1 | 2 | 7.6 | 25.5 | 14.4* |
| First layer only | 1 | 12.4 | 13.3 | 13.1 |
| | 2 | 13.8 | 13.2 | 12.3 |

*when the reservior emptied the moisture vapor transmission began to fall.

The first and second layers were impermeable to liquid water and were conformable.

EXAMPLE 2

The procedure of Example 1 was followed except that a 1.1 mil (28 micron) "Hytrel" 4056 Brand polyester elastomer (E. I. duPont de Nemours & Co., Wilmington, Del.) film was prepared and utilized. Twenty-five grams per square meter of adhesive prepared in accordance with U.S. Pat. No. 4,323,557 comprising a copolymer of 89% by weight of isooctylacrylate, 8.8% of N-vinyl pyrrolidone, 1% iodine USP and 1.2% of sodium iodine USP was applied to the surface of the film. A release liner of 78 pounds (127 g/m$^2$) bleached one side coated polyethylene silicone paper (Polyslik S-80053 (H. P. Smith Co., Chicago, Ill.) was applied to the adhesive side of the film. The clay-coated kraft carrier was die cut and the center removed as in Example 1. In this case, one 1/32" (0.08 cm) hole was punched in the center of the first layer, i.e., adhesive coated film. A second layer of the same film was applied to the nonadhesive side of the first layer as in Example 1. The following results were obtained via in vitro testing of the samples:

| moisture vapor permeability (in vitro) | first layer (singly) | 810 g/m$^2$/24 hr/ 80% relative humidity differential/40° C. |
|---|---|---|
| | second layer (singly) | 1100 g/m$^2$/24 hr/80% relative humidity differential/40° C. |

The first and second layers were impermeable to liquid water and conformable.

EXAMPLE 3

A dressing was prepared in accordance with Example 1 using porous polypropylene (Celgard No. 3501, Celanese Corporation, Charlotte, N.C. 28232) as the first layer. Twenty-five grams per square meter of the adhesive of Example 1 was coated on a silicone liner comprising 80 pound (130.5 g/m$^2$) bleached two side coated, silicone paper (2-80BKG-157, Daubert Chemical Co., Dixon, Ill.) using a standard horizontal laboratory knife coater. The adhesive was then dry laminated to the polypropylene between two squeeze rolls on a Laminex Model 12 V Machine (Laminex, Inc., Matthews, N.C.) to complete the formation of the first layer. Patches measuring 10 cm×10 cm were cut out and a 0.08 cm hole was punched through the center. A second layer 5 cm×5 cm in size as described in Example 1 was adhered to the first layer in the following manner. A bead of the adhesive of Example 1 was placed on the edges of the 5 cm×5 cm second layer, and said layer centered on the nonadhesive side of the polypropylene layer. The following in vitro data was obtained on the prepared samples:

| moisture vapor permeability (in vitro) | first layer (singly) | 1100 g/m²/24 hr/80% relative humidity differential/40° C. |
|---|---|---|
| | second layer (singly) | 1200 g/m²/24 hr/80% relative humidity differential/40° C. |

The first and second layers were impermeable to liquid water and conformable with the second layer being more conformable than the first layer.

EXAMPLE 4

A wound dressing was prepared in accordance with Example 1 except that a pad of 8 ply cotton gauze (Johnson and Johnson, New Brunswick, N.J.) was included in the space between the first and second layers. The in vitro results obtained were the same as with those in Example 1. The in vivo results were as follows:

| | Moisture Vapor Transmission (in vivo on pig wounds as in Example 1) | | |
|---|---|---|---|
| | (g/m²/hr) | | |
| Sample Type | 24 Hours | 48 Hours | 72 Hours |
| Example 1 | 18.2 | 20.9 | 19.1 |
| Example 2 | 32.8 | 29.7 | 27.7 |

The first and second layers were impermeable to liquid water and conformable.

EXAMPLE 5

A wound dressing was made in accordance with Example 4 except that the gauze was replaced with a pad of blown polypropylene microfibers made in accordance with U.S. Pat. No. 4,118,531, impregnated with a wound treatment material comprising Dextran crosslinked with epichlorohydrin made in accordance with U.S. Pat. No. 4,225,580 (Debrisan brand, Johnson and Johnson, New Brunswick, N.J.). The in vitro results obtained were the same as with those in Example 1. The first and second layers were impermeable to liquid water and conformable.

EXAMPLE 6

Using a Model 12 BS Rando-Web machine (Rando Machine Corp., Macedon, N.Y.) a nonwoven fabric or web was made from 1.5 denier, 1.5 inch (3.8 cm) rayon fibers (sold by Avtex Inc. of N.Y.) and QY4391 acrylic binder (sold by K. J. Quinn Co. Inc. of Malden, Mass.) which was applied as an aqueous emulsion (concentration: 26% solids) by means of coater rolls situated after the web-forming station and before the drying station. Conventional operating procedures were used throughout. After drying at 145° for 4 minutes, the fabric had a fiber weight of 21.2 grams per square meter and a total weight of 42.4 grams per square meter. Forty-six grams per square meter of an adhesive prepared using a polymer of 96% units of isooctylacrylate and 4% units of acrylic acid were coated onto a release liner comprising 80 pound (130.5 grams per square meter) bleached, two side coated, silicone paper (2-80BKG-157, Daubert Chemical Co., Dixon, Ill.) using a standard horizontal laboratory knife coater. The adhesive was then dry laminated to the fabric between two squeeze rolls on a Laminex Model 12V machine (Laminex, Inc., Matthews, N.C.). The adhesive was not liquid water permeable. Patches measuring 10 cm × 10 cm were cut out and a 0.08 cm hole was punched through the center. A second layer 5 cm × 5 cm in size as described in Example 1 except that it was 0.74 mil (19 microns) thick was heat sealed to the adhesive of the adhesive/web first layer on the web side through the web and surrounding the hole.

| moisture vapor permerability (in vitro) | first layer (singly) | 1000 g/m²/24 hrs/80% relative humidity differential/40° C. |
|---|---|---|
| | second layer (singly) | 1200 g/m²/24 hrs/80% relative humidity differential/40° C. |

The first and second layers were impermeable to liquid water and conformable with the second layer being more conformable than the first.

EXAMPLE 7

A wound dressing was prepared having the configuration shown in FIG. 5 using the same materials as in Example 1. The in vitro moisture vapor permeability of the first and second layer was, therefore, the same as in Example 1. The first layer was prepared in accordance with Example 1 except that a 1/16" (0.16 cm) hole was punched in the center of the first layer. The second layer was made from two 5 cm × 5 cm films of the same material as Example 1. A 1/16" (0.16 cm) hole was punched in the center of one of the 5 cm × 5 cm films. This lower portion of the second layer was heat sealed to the first layer on the nonadhesive side using a heated mandrel so that the 1/16" (0.16 cm) holes were lined up and a ⅛" (0.3 cm) to ¼" (0.6 cm) weld forms around the holes. The other or 5 cm × 5 cm film (upper portion) was then heat sealed to the lower portion around the periphery of each with the heat sealer of Example 1. The first and second layers were impermeable to liquid water and conformable.

EXAMPLE 8

A wound dressing was made in accordance with Example 7 except that into the reservoir between the upper and lower portions of the second layer was placed a piece of 8 ply cotton gauze (Johnson and Johnson, New Brunswick, N.J.). The in vitro moisture vapor permeabilities were the same as in Examples 1 and 7 because the same films were used. The first and second layers were impermeable to liquid water and conformable.

EXAMPLE 9

The first layer of Example 1, i.e., film and adhesive, was tested for comparison with wound dressings prepared in accordance with Example 1, Example 7 and Example 8. A sample of each was applied over a hole containing a rubber septum in a steel plate. A syringe was used to place 3 cubic centimeters of distilled water containing blue dye under each of the dressings by passing the syringe through the septum and injecting the water under the dressing allowing the water to flow into the reservoir. The time for the water to evaporate was recorded. The dressings were checked each hour. Results were as follows:

Evaporation was significantly greater with the reservoir wound dressing and was the greatest with the wound dressing of FIG. 5.

| First layer - Example 1 | 28 hours |
| Example 1 - wound dressing | 19 hours |
| Example 7 | 12 hours |
| Example 8 | 13 hours |

EXAMPLE 10

A roll of wound dressings was prepared having the configuration shown in FIG. 7 and utilizing films made in accordance with Example 1. The adhesive coating techniques and adhesive of Example 1 were utilized. A silicone release liner (1-65BKG-157, Daubert Chemical Co.) was applied to the first layer. The holes included in the first layer were made using a 3/16" (0.5 cm) die at a 2 inch (5 cm) hole spacing. The releasable layer was removed from the first layer. The second layer of film with its releasable layer attached was placed over the first layer on the nonadhesive side of the first layer. The two films were heat sealed by means of continuous line heat sealer to form the pattern shown in FIG. 7 and the releasable layer removed. The holes in the first layer were approximately in the center of each of the separate wound dressings. Individual wound dressings were removed from the roll by cutting between the double rows of heat seals. Dressings were cut from the roll and applied to the test device described in Example 9. The first and second layers were impermeable to liquid water and conformable.

What is claimed is:

1. A wound dressing comprising at least two films, each of which is conformable to anatomical surfaces, the first of said films adapted to be placed over a wound surface having a moisture vapor permeability of at least 300 grams per square meter per 24 hours at an 80 percent relative humidity differential at 40° C., being impermeable to liquid water throughout substantially its entire imperforate area, and containing at least one perforation therein positioned for passing wound exudate therethrough; said first film having a pressure sensitive adhesive on the wound contacting surface thereof for attaching said dressing to anatomical surfaces;

the second of said films being imperforate, impermeable to liquid water, and having a moisture vapor permeability of at least 600 grams per square meter per 24 hours at an 80 percent relative humidity differential at 40° C., said second film overlying said first film and being attached at its periphery to said first film on the side opposite to that having said pressure-sensitive adhesive thereon, and extending over an area surrounding said at least one perforation;

said dressing providing a reservoir between said first and second films into which excess exudate can pass and be evaporated to the ambient environment.

2. The wound dressing of claim 1 wherein said first film includes peripheral portions extending beyond the periphery of said second layer.

3. The wound dressing of claim 2 which includes a release liner attached to the surface of said first film having said pressure sensitive adhesive thereon, and a releasable layer attached to the surface of said first film opposite to the surface having said pressure sensitive adhesive thereon and attached to said peripheral portions of said first film, said releasable layer being attached to said first film more tenaciously than the release liner is attached to the adhesive surface of said first film.

4. The wound dressing of claim 3 in which said releasable layer comprises a frame attached to said peripheral portions of said first film.

5. The wound dressing of claim 1 wherein the reservoir in said wound dressing contains a member selected from the group comprising a medicament, an absorbent material and mixtures thereof.

6. A wound dressing comprising at least two films, each of which is conformable to anatomical surfaces, the first of said films adapted to be placed over a wound surface having a moisture vapor permeability of at least 300 grams per square meter per 24 hours at an 80 percent relative humidity differential at 40° C., being impermeable to liquid water throughout substantially its entire imperforate area, and containing a perforation therein positioned for passing wound exudate therethrough; said first film having a pressure sensitive adhesive on the wound contacting surface thereof for attaching said dressing to anatomical surfaces;

the second of said films having a moisture vapor permeability of at least 600 grams per square meter per 24 hours at an 80 percent relative humidity differential at 40° C., being impermeable to liquid water throughout substantially its, entire imperforate area and comprising an upper portion of polymeric imperforate film and a lower portion of polymeric film attached at the periphery thereof to the periphery of said upper portion and containing a perforation therein of substantially corresponding size to the perforation in said first film for passing wound exudate therethrough, said lower portion overlying said first film and being attached at the periphery of its perforation to said first film on the side opposite to that having the pressure sensitive adhesive thereon around the periphery of said perforation in said first film; said dressing providing a reservoir between said upper and lower portions of said second film into which excess exudate can pass and be evaporated to the ambient environment.

7. A wound dressing comprising:
(a) a first layer adapted to be placed over a wound surface which is conformable to animal anatomical surfaces, has a moisture vapor permeability of at least 300 grams per square meter per 24 hours at an 80% relative humidity differential at 40° C., is impermeable to liquid water throughout substantially its entire imperforate area, and contains perforation means therein positioned for passing wound exudate through said first layer means for adhering said first layer to said anatomical surfaces; and
(b) a second layer which is imperforate, is conformable to animal anatomical surfaces, is impermeable to liquid water, and has a moisture vapor permeability of at least 600 grams per square meter per 24 hours at an 80% relative humidity differential at 40° C., said second layer overlaying said first layer and being attached at its periphery to said first layer on the side opposite to that which contacts the wound surface and extending over an area surrounding said perforation means to provide a reservoir into which exudate from a wound can pass and be at least partially evaporated therefrom; whereby (c) said moisture vapor permeability of said first and second layers and the size of said perforation means being controlled so as to allow the wound to heal under moist conditions without significant scab formation.

8. The wound dressing of claim 7 wherein said perforation means comprise at least one hole having a diameter in the range of 0.08 to 0.64 cm.

9. A plurality of wound dressings in roll form, each of said dressings comprising at least two films, each of which films is conformable to anatomical surfaces, the first of said films adapted to be placed over a wound surface having a moisture vapor permeability of at least 300 grams per square meter per 24 hours at an 80 percent relative humidity differential at 40° C., being impermeable to liquid water throughout substantially its entire imperforate area, and containing at least one perforation therein positional for passing wound exudate therethrough; said first film having a pressure sensitive adhesive on the wound contacting surface thereof for attaching said dressing to anatomical surfaces;

the second of said films being imperforate, impermeable to liquid water, and having a moisture vapor permeability of at least 600 grams per square meter per 24 hours at an 80 percent relative humidity differential at 40° C., said second film overlying said first film and being attached at its periphery to said first film on the side opposite to that having said pressure-sensitive adhesive thereon, and extending over an area surrounding said at least one perforation;

said dressing providing a reservoir between said first and second films into which excess exudate can pass and be evaporated to the ambient environment, and a release liner removably attached to the surface of said first film having said pressure sensitive adhesive thereon.

10. A method for healing a wound comprising:

1. attaching over the surface of the wound a wound dressing comprising at least two films, each of which is conformable to anatomical surfaces, the first of said films adapted to be placed over a wound surface having a moisture vapor permeability of at least 300 grams per square meter per 24 hours at an 80 percent relative humidity differential at 40° C., being impermeable to liquid water throughout substantially its entire imperforate area, and containing at least one perforation therein positioned for passing wound exudate therethrough; said first film having a pressure sensitive adhesive on the wound contacting surface thereof for attaching said dressing to anatomical surfaces;

the second of said films being imperforate, impermeable to liquid water, and having a moisture vapor permeability of at least 600 grams per square meter per 24 hours at an 80 percent relative humidity differential at 40° C., said second film overlying said first film and being attached at its periphery to said first film on the side opposite to that having said pressure-sensitive adhesive thereon, and extending over an area surrounding said at least one perforation;

said dressing providing a reservoir between said first and second films into which excess exudate can pass and be evaporated to the ambient environment;

2. allowing exudate from the wound to pass through said at least one perforation in said first film of said wound dressing into said reservoir and 3. allowing moisture from said exudate to evaporate from said reservoir through said second film to the ambient environment.

* * * * *